United States Patent

Roch et al.

[11] Patent Number: 4,714,698
[45] Date of Patent: Dec. 22, 1987

[54] 8-ALKYLTHIO-2-PIPERAZINO-PYRIMIDO[5,4-D]-PYRIMIDINES

[75] Inventors: Josef Roch; Armin Heckel; Josef Nickl; Erich Muller; Berthold Narr, all of Biberach; Rainer Zimmermann, Mittelbiberach; Johannes Weisenberger, Biberach, all of Fed. Rep. of Germany

[73] Assignee: Dr. Karl Thomae GmbH, Riss, Fed. Rep. of Germany

[21] Appl. No.: 745,095

[22] Filed: Jun. 17, 1985

[30] Foreign Application Priority Data

Jun. 22, 1984 [DE] Fed. Rep. of Germany ....... 3423092

[51] Int. Cl.⁴ ................... A61K 31/505; C07D 471/04
[52] U.S. Cl. .................................. 514/212; 514/258; 540/600; 544/256
[58] Field of Search ................ 544/256; 514/258, 212; 540/600

[56] References Cited

U.S. PATENT DOCUMENTS

| | | | |
|---|---|---|---|
| 3,031,450 | 4/1962 | Fischer et al. | 544/256 |
| 3,322,755 | 5/1967 | Roch et al. | 544/256 |
| 3,562,265 | 2/1971 | Murakami et al. | 544/256 |
| 4,478,833 | 10/1984 | Roch et al. | 544/256 |
| 4,518,596 | 5/1985 | Roch et al. | 514/232 |

OTHER PUBLICATIONS

Burger, A., *Medicinal Chemistry*, 2nd Ed., (1960), Interscience Publishers, Inc., New York, N.Y., pp. 1080, 1082–1083.

*Primary Examiner*—Donald G. Daus
*Assistant Examiner*—Mark W. Noel
*Attorney, Agent, or Firm*—David Frankhouser; Alan R. Stempel; Mary Ellen Timbers

[57] ABSTRACT

The invention relates to new compounds of general formula

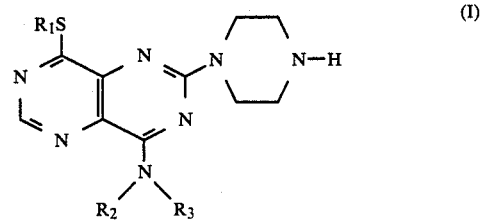

wherein
$R_1$ represents an alkyl group,
$R_2$ represents a hydrogen atom, an alkyl group optionally substituted (except at the $\alpha$ carbon atom) by a hydroxy group, or represents a cycloalkyl group or an allyl, phenyl or benzyl group,
$R_3$ represents an allyl group, an alkyl group optionally substituted (except at the $\alpha$ carbon atom) by a hydroxy group, or represents a cycloalkyl group or
$R_2$ and $R_3$ together with the nitrogen atom between them represent a straight-chained alkyleneimino group, the acid addition salts thereof, particularly the acid addition salts thereof with physiologically acceptable inorganic or organic acids which have valuable pharmacological properties, particularly a metastasis-inhibiting effect based on their selective tumour-PDE inhibiting effect, and pharmaceutical compositions containing these compounds or the physiologically acceptable acid addition salts thereof.

The new compounds may be prepared according to methods known for analogous compounds.

5 Claims, No Drawings

8-ALKYLTHIO-2-PIPERAZINO-PYRIMIDO[5,4-D]-PYRIMIDINES

No. EP-A-0,023,559 equivalent to U.S. Pat. No. 4,518,596 describes trisubstituted 2-piperazino-pyramido[5,4-d]pyrimidines which have valuable pharmacological properties, particularly an antithrombotic activity, a phosphodiesterase inhibitory effect and an inhibitory effect on the aggregation of cancer cells washed into the bloodstream.

Surprisingly, it has now been found that the new 8-alkylthio-2-piperazino-pyrimido[5,4-d]pyrimidines of the formula

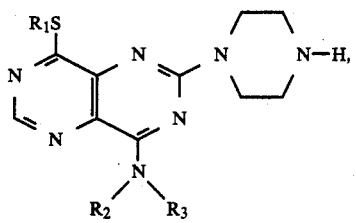

(I)

which differ from the compounds of EP-No.-A-0,023,559 by the substituent in the 4-position, have superior pharmacological properties, particularly a metastasis-inhibiting activity, based on their selective tumour-PDE-inhibiting activity, and an inhibitory effect on tumour growth.

The present invention relates to the new compounds of the formula I above, the acid addition salts thereof, particularly the acid addition salts with physiologically acceptable inorganic or organic acids, pharmaceutical compositions containing these compounds or the physiologically acceptable acid addition salts thereof and processes for preparing them.

In the formula I above $R_1$ represents an alkyl group containing 1 to 3 carbon atoms, $R_2$ represents a hydrogen atom, an alkyl group containing 1 to 6 carbon atoms optionally substituted (except at the α carbon atom) by a hydroxy group, a cycloalkyl group containing 5 to 7 carbon atoms or an allyl, phenyl or benzyl group, $R_3$ represents an allyl group, an alkyl group containing 1 to 6 carbon atoms optionally substituted (except at the α carbon atom) by a hydroxy group or a cycloalkyl group containing 5 to 7 carbon atoms or $R_2$ and $R_3$ together with the nitrogen atom between them represent a straight-chained alkyleneimino group containing 2 to 8 carbon atoms.

As examples of the definitions of the groups $R_1$ to $R_3$ given hereinbefore:

$R_1$ may represent a methyl, ethyl, n-propyl or isopropyl group and

may represent a methylamino, ethylamino, n-propylamino, isopropylamino, n-butylamino, isobutylamino, tert.butylamino, n-pentylamino, isopentylamino, tert.pentylamino, n-hexylamino, dimethylamino, diethylamino, di-n-propylamino, di-n-butylamino, di-n-pentylamino, di-n-hexylamino, diisopropylamino, N-methyl-ethylamino, N-methylisopropylamino, N-ethyl-n-propylamino, cyclopentylamino, cyclohexylamino, cycloheptylamino, dicyclopentylamino, dicyclohexylamino, dicycloheptylamino, N-cyclopentylcyclohexylamino, 2-hydroxyethylamino, 3-hydroxy-n-propylamino, 4-hydroxy-n-butylamino, 6-hydroxy-n-hexylamino, 2-hydroxy-n-propylamino, di(2-hydroxyethyl)-amino, di(3-hydroxy-n-propyl)-amino, di(2-hydroxy-n-propyl)-amino, di(6-hydroxy-n-hexyl)-amino, N-methyl-cyclopentylamino, N-methyl-cyclohexylamino, N-ethylcyclohexylamino, N-isopropyl-cycloheptylamino, N-n-hexylcyclohexylamino, N-(2-hydroxyethyl)-cyclohexylamino, N-(2-hydroxy-n-propyl)-cyclopentylamino, N-(3-hydroxy-n-propyl)-cycloheptylamino, N-(6-hydroxy-n-hexyl)-cyclohexylamino, allylamino, phenylamino, benzylamino, diallylamino, N-methyl-allylamino, N-ethyl-allylamino, N-isopropyl-allylamino, N-(2-hydroxyethyl)-allylamino, N-methyl-phenylamino, N-ethyl-phenylamino, N-n-hexylphenylamino, N-(2-hydroxy-ethyl)-phenylamino, N-(3-hydroxy-n-propyl)-phenylamino, N-(6-hydroxy-n-hexyl)-phenylamino, dibenzylamino, N-methylbenzylamino, N-ethylbenzylamino, N-n-propyl-benzylamino, N-n-hexyl-benzylamino, N-(2-hydroxyethyl)-benzylamino, N-(3-hydroxy-n-propyl)-benzylamino, N-(6-hydroxy-n-hexyl)-benzylamino, N-allyl-cyclohexylamino, N-allyl-benzylamino, dimethyleneimino, trimethyleneimino, pyrrolidino, piperidino, hexamethyleneimino, heptamethyleneimino or octamethyleneimino group.

However, the preferred compounds of formula I are those wherein $R_1$ is as hereinbefore defined, $R_2$ represents a hydrogen atom, an allyl group or an alkyl group containing 1 to 4 carbon atoms, $R_3$ represents an alkyl group containing 1 to 6 carbon atoms, an allyl, cyclohexyl, phenyl, benzyl, 2-hydroxyethyl, 2-hydroxy-n-propyl or 3-hydroxy-n-propyl group or $R_2$ and $R_3$ together with the nitrogen atom between them represent a pyrrolidino, piperidino, hexamethyleneimino or heptamethyleneimino group, but particularly the compounds of formula I wherein $R_1$ represents a methyl group, $R_2$ represents a hydrogen atom or a methyl or ethyl group, $R_3$ represents an alkyl group containing 1 to 6 carbon atoms or $R_2$ and $R_3$ together with the nitrogen atom between them represent a pyrrolidino, piperidino or hexamethyleneimino group, and the acid addition salts thereof, more particularly the physiologically acceptable acid addition salts thereof.

According to the invention, the new compounds of formula I above are obtained by reacting a pyrimido[5,4-d]pyrimidine of formula

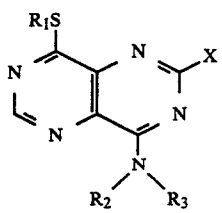

(II)

wherein
$R_1$ to $R_3$ are as hereinbefore defined and
X represents a nucleofugic leaving group such as a halogen atom, e.g. a chlorine or bromine atom, a substituted hydroxy group, e.g. the phenoxy group, or a sulphonyl group, e.g. the methanesulphonyl group, with a piperazine of general formula

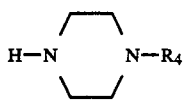

(III)

wherein
$R_4$ represents a hydrogen atom or an easily removable protecting group such as the trimethylsilyl group, an alkoxycarbonyl group, e.g. the carbethoxy group, or an alkanoyl group, e.g. the formyl or acetyl group, and if necessary subsequently splitting off any protecting group used.

The reaction is appropriately carried out in an inert solvent such as acetone, methylene chloride, chloroform, tetrahydrofuran, dioxane, dimethylformamide or dimethylsulphoxide, optionally in the presence of an inorganic base such as sodium carbonate or potassium hydroxide or a tertiary organic base such as triethylamine or pyridine, whilst the latter may also be used as solvent, at temperatures of between 0° and 120° C., but preferably at temperatures of between 20° and 50° C. However, the reaction may also be carried out without a solvent or in the presence of an excess of the compounds of formula III used.

The optional subsequent splitting off of any protecting group used is preferably carried out hydrolytically in the presence of an acid or base in an aqueous solvent such as water/methanol or water/ethanol and preferably at the boiling temperature of the reaction mixture.

The compounds of formula I thus obtained may, if desired, subsequently be converted into the acid addition salts thereof, particularly the acid addition salts with physiologically acceptable inorganic or organic acids. Examples of such acids include hydrochloric, hydrobromic, sulphuric, phosphoric, methanesulphonic, p-toluenesulphonic, acetic, lactic, citric, tartaric, succinic, maleic, fumaric and salicylic acid.

The compounds of formula II used as starting materials may be obtained, for example, by step-wise replacement of the chlorine atoms of 2,4,8-trichloropyrimido[5,4-d]pyrimidine, in which first of all the chlorine atom in position 4 is exchanged, then the chlorine atom in position 8 is exchanged by methods known per se.

As already mentioned hereinbefore, the new compounds of general formula I and the physiologically acceptable acid addition salts thereof have valuable pharmacological properties, not only an antithrombotic activity but, more particularly, an inhibiting effect on metastasis and tumour growth, on account of their selective tumour-PDE inhibiting activity.

For example, the following compounds:
A = 8-Methylthio-2-piperazino-4-pyrrolidino-pyrimido[5,4-d]pyrimidine,
B = 4-Diethylamino-8-methylthio-2-piperazino-pyrimido[5,4-d]pyrimidine,
C = 4-n-Hexylamino-8-methylthio-2-piperazino-pyrimido[5,4-d]pyrimidine and
D = 4-Hexamethyleneimino-8-methylthio-2-piperazinopyrimido[5,4-d]pyrimidine were tested as follows for their inhibiting effect on tumour cells:

(a) Obtaining the enzyme

The phosphodiesterase was obtained from B16 melanoma tissue from mice by centrifuging the homogenised tissue at $5000 \times g$ (15 minutes at 4° C.). The tissues were homogenized by repeated freezing and thawing and homogenisation according to Potter-Elvehjem or by ultrasound. The homogenised supernatant containing the PDE was deep frozen and stored in batches at −25° C.

Phosphodiesterase was obtained from human thrombocytes by an analogous method.

(b) Determining the PDE inhibition (PDE assay)

The PDE inhibition by the test substances was determined using 1 $\mu$mol/l of $^3$H-cAMP as substrate. The PDE inhibition was determined by measuring the degradation of the substrate $^3$H-cAMP used into $^3$H-AMP by comparison with the control without the test substance. The $^3$H-AMP formed was separated from the remaining $^3$H-cAMP by precipitation with zinc sulphate-barium hydroxide.

The $ED_{50}$, i.e. the concentration which inhibited the PDE activity by 50%, was calculated by linear regression analysis.

The results of these tests are shown in the following table:

| | PDE inhibition $ED_{50}$ ($\mu$mol/l) | |
|---|---|---|
| Substance | Human thrombocytes | $B_{16}$ tumour cells |
| A | 1.6 | 0.066 |
| B | 1.3 | 0.037 |
| C | 1.2 | 0.12 |
| D | 1.7 | 0.028 |

Moreover, the new compounds are well tolerated. Thus, for example, when substance A was administered to mice in a dosage of 20 mg/kg i.v. or 100 mg/kg p.o., none of the 10 animals used died.

In view of their pharmacological properties, the compounds of general formula I and the acid addition salts thereof with physiologically acceptable inorganic or organic acids are suitable for the prophylaxis of thromboembolic diseases such as coronary infarct, cerebral infarct, so-called transient ischaemic attacks and amaurosis fugax, and for the prophylaxis of arteriosclerosis and metastasis and for inhibiting tumour growth.

The dosage required to obtain these effects is appropriately 0.1 to 4 mg/kg of body weight, preferably 0.2 to 3 mg/kg of body weight, 2 to 4 times a day. The compounds of general formula I prepared according to the invention and the physiologically acceptable acid addition salts thereof with inorganic or organic acids, optionally combined with other active substances, may be processed with one or more conventional inert carriers and/or diluents, e.g. corn starch, lactose, glucose, microcrystalline cellulose, magnesium stearate, polyvinylpyrrolidone, citric acid, tartaric acid, water, water-/ethanol, water/glycerol, water/sorbitol, non-ionic surfactants such as polyoxyethylene fatty acid esters, water-polyethylene glycol, propyleneglycol, cetylstearyl alcohol, carboxymethylcellulose or fatty substances such as hard fat or suitable mixtures thereof, and incorporated in conventional galenic preparations such as plain or coated tablets, capsules, powders, suspensions, drops, ampoules, syrups or suppositories.

The Examples which follow are intended to illustrate the invention:

EXAMPLE A 2,8-Dichloro-4-pyrollidino-pyrimido[5,4-d]pyrimidine 4.7 g (0.02 mol) of 2,4,8-trichloro-pyrimido[5,4-d]pyrimidine is dissolved in 200 ml of chloroform, cooled to 5° C. and mixed with 3.4 g (0.04 mol) of sodium hydrogencarbonate in 40 ml of water. Then 1.65 ml (0.02 mol) of pyrrolidine in 20 ml of chloroform lis added dropwise and the solution is stirred for 15 minutes at 5° C. and for 30 minutes at ambient temperature. The organic phase is then separated off, washed with 100 ml of water, dried over sodium sulphate, and concentrated by evaporation in a rotary evaporator.

Yield: 4.7 g (87% of theory),
M.p.: 144°–146° C. (ethanol).

The following compounds are obtained analogously:
2,8-Dichloro-4-piperidino-pyrimido[5,4-d]pyrimidine
M.p.: 114°–117° C. (ethanol).
2,8-Dichloro-4-hexamethyleneimino-pyrimido[5,4-d]pyrimidine
M.p.: 121°–123° C. (methanol).
2,8-Dichloro-4-dimethylamino-pyrimidino[5,4-d]pyrimidine
M.p.: 161°–163° C. (ethyl acetate).
2,8-Dichloro-4-diethylamino-pyrimido[5,4-d]pyrimidine
M.p.: 113°–114° C. (ethanol).
2,8-Dichloro-4-di-n-propylamino-pyrimido[5,4-d]pyrimidine
M.p.: 51°–52° C.
2,8-Dichloro-4-di-n-butylamino-pyrimido[5,4-d]pyrimidine
M.p.: 47°–49° C.
2,8-Dichloro-4-(N-cyclohexyl-methylamino)-pyrimido[5,4-d]pyrimidine
M.p.: 143°–145° C.
4-(N-Benzyl-methylamino)-2,8-dichloro-pyrimido[5,4-d]pyrimidine
M.p.: 136°–138° C.
2,8-Dichloro-4-(N-methyl-phenylamino)-pyrimido[5,4-d]pyrimidine
M.p.: 208°–209° C.
2,8-Dichloro-4-(N-ethyl-3'-hydroxy-n-propylamino)-pyrimido[5,4-d]pyrimidine
M.p.: 70°–72° C.
2,8-Dichloro-4-methylamino-pyrimido[5,4-d]pyrimidine
M.p.: 196°–197° C. (ethyl acetate/methanol).
2,8-Dichloro-4-n-hexylamino-pyrimido[5,4-d]pyrimidine
M.p.: 78°–80° C. (petroleum ether).
2,8-Dichloro-4-heptamethyleneimino-pyrimido[5,4-d]pyrimidine
M.p.: 129°–131° C.
2,8-Dichloro-4-(N-methyl-ethylamino)-pyrimido[5,4-d]pyrimidine
M.p.: 108°–110° C.
4-Diallylamino-2,8-dichloro-pyrimido[5,4-d]pyrimidine
M.p.: 127°–129° C.

EXAMPLE B

2-Chloro-8-methylthio-4-pyrrolidino-pyrimido[5,4-d]pyrimidine 4.7 g (0.02 mol) of 2,8-dichloro-4-pyrrolidino-pyrimido[5,4-d]pyrimidine is dissolved in 200 ml of dioxan/methanol (1:1) and mixed with a solution of 0.46 g (0.02 mol) of sodium and 2.2 ml (0.04 mol) of methyl-mercaptan in 50 ml of methanol at 5° C. The mixture is stirred at 5° C. for 15 minutes and then for 30 minutes at ambient temperature. The suspension obtained is added to 500 ml of water. The precipitate obtained is suction filtered, washed with water and dried.

Yield: 96.2% of theory,
M.p.: 188°–191° C. (ethyl acetate).

EXAMPLE C

2-Chloro-8-methylthio-4-piperidino-pyrimido[5,4-d]pyrimidine 4.26 g (15 mmol) of 2,8-dichloro-4-piperidino-pyrimido[5,4-d]pyrimidine is dissolved in 150 ml of acetone and cooled to 0° C. At this temperature, a solution of 0.35 g (15 mmol) of sodium in 25 ml of methanol with 0.85 ml (15 mmol) of methyl mercaptan is added dropwise. The mixture is then stirred for 30 minutes with cooling. After the resulting solution has been evaporated, the residue is taken up in 300 ml of methylene chloride. It is washed twice with 100 ml of water, the organic phase is dried over sodium sulphate and concentrated by evaporation.

Yield: 3.9 g (88% of theory),
M.p.: 135°–136° C. (ethanol).

The following compounds are obtained analogously:
2-Chloro-8-ethylthio-4-piperidino-pyrimido[5,4-d]pyrimidine
M.p.: 110°–111° C. (ethanol).
2-Chloro-4-piperidino-8-n-propylthio-pyrimido[5,4-d]pyrimidine
M.p.: 107°–109° C. (ethanol).
2-Chloro-4-hexamethyleneimino-8-methylthio-pyrimido[5,4-d]pyrimidine
M.p.: 173°–175° C. (dioxane).
2-Chloro-4-dimethylamino-8-methylthio-pyrimido[5,4-d]pyrimidine
M.p.: 166°–168° C. (ethyl acetate).
2-Chloro-4-diethylamino-8-methylthio-pyrimido[5,4-d]pyrimidine
M.p.: 90°–91° C. (methanol).
2-Chloro-4-di-n-propylamino-8-methylthio-pyrimido[5,4-d]pyrimidine
M.p.: 92°–94° C.
2-Chloro-4-di-n-butylamino-8-methylthio-pyrimido[5,4-d]pyrimidine
M.p.: 42°–44° C.
2-Chloro-4-(N-cyclohexyl-methylamino)-8-methylthio-pyrimido[5,4-d]pyrimidine
M.p.: 135°–137° C. (ethanol).
4-(N-Benzyl-methylamino)-2-chloro-8-methylthio-pyrimido[5,4-d]pyrimidine
M.p.: 93° C. (sintering).
2-Chloro-4-(N-methyl-phenylamino)-8-methylthio-pyrimido[5,4-d]pyrimidine M.p.: 183°–184° C. (methanol).

2-Chloro-4-(N-ethyl-3'-hydroxy-n-propylamino)-8-methylthio-pyrimido[5,4-d]pyrimidine
Sinters from 66° C.

2-Chloro-4-methylamino-8-methylthio-pyrimido[5,4-d]pyrimidine
M.p.: 233°–234° C. (dioxane/water 1:1).

2-Chloro-4-hexylamino-8-methylthio-pyrimido[5,4-d]pyrimidine
M.p.: 80°–82° C. (methanol).

2-Chloro-4-heptamethyleneimino-8-methylthio-pyrimido[5,4-d]pyrimidine
M.p.: 124°–125° C. (methanol).

2-Chloro-4-(N-methyl-ethylamino)-8-methylthio-pyrimido[5,4-d]pyrimidine
M.p.: 107°–109° C.

2-Chloro-4-diallylamino-8-methylthio-pyrimido[5,4-d]pyrimidine
M.p.: 83°–84° C. (methanol).

EXAMPLE 1

8-Methylthio-2-piperazino-4-pyrrolidino-pyrimido[5,4-d]pyrimidine 2.8 g (0.01 mol) of 2-chloro-8-methylthio-4-pyrrolidino-pyrimido[5,4-d]pyrimidine is dissolved warm in 300 ml of dimethylsulphoxide and then a solution of 4.3 g (0.05 mol) of piperazine is added. After being stirred for 1 hour at ambient temperature the solution is poured into 1.5 liters of water. The precipitate obtained is suction filtered, washed with water and dried.
Yield: 3 g (90% of theory).

For further purification, the product is dissolved in 500 ml of 0.1N hydrochloric acid and reprecipitated with conc. ammonia.
M.p.: 188°–189° C.

EXAMPLE 2

8-Methylthio-4-piperidino-2-piperazino-pyrimido[5,4-d]pyrimidine 2.0 g (6.8 mmol) of 2-chloro-8-methylthio-4-piperidino-pyrimido[5,4-d]pyrimidine is dissolved warm in 70 ml of dimethylsulphoxide and stirred with a solution of 6 g of piperazine in 70 ml of dimethylsulphoxide for 1 hour at ambient temperature. Then the solution is poured into 1 liter of water, the precipitate obtained is suction filtered and washed with water. The residue is taken up in 50 ml of methylene chloride and extracted with 50 ml of 0.05N sodium hydroxide solution. The organic phase is separated off, dried over sodium sulphate and concentrated in a rotary evaporator.
Yield: 1.1 g (47% of theory),
M.p.: 159°–160° C.

EXAMPLE 3

8-Ethylthio-4-piperidino-2-piperazino-pyrimido[5,4-d]pyrimidine

Prepared analogously to Example 2 from 2-chloro-8-ethylthio-4-piperidino-pyrimido[5,4-d]pyrimidine and piperazine in dimethylsulphoxide.
Yield: 57% of theory,
M.p.: 130°–131° C.

EXAMPLE 4

4-Piperidino-2-piperazino-8-n-propylthio-pyrimido[5,4-d]-pyrimidine

Prepared analogously to Example 2 from 2-chloro-4-piperidino-8-n-propylthio-pyrimido[5,4-d]pyrimidine and piperazine in dimethylsulphoxide.
Yield: 69% of theory,
M.p.: 144°–146° C.

EXAMPLE 5

4-Hexamethyleneimino-8-methylthio-2-piperazino-pyrimido[5,4-d]pyrimidine

Prepared analogously to Example 2 from 2-chloro-4-hexamethyleneimino-8-methylthio-pyrimido[5,4-d]pyrimidine and piperazine in dimethylsulphoxide.
Yield: 54% of theory,
M.p.: 124°–126° C. (methanol).

EXAMPLE 6

4-Dimethylamino-8-methylthio-2-piperazino-pyrimido[5,4-d]pyrimidine

Prepared analogously to Example 2 from 2-chloro-4-dimethylamino-8-methylthio-pyrimido[5,4-d]pyrimidine and piperazine in dimethylsulphoxide.
Yield: 91% of theory,
M.p.: 166°–168° C. (ethyl acetate).

EXAMPLE 7

4-Diethylamino-8-methylthio-2-piperazino-pyrimido[5,4-d]pyrimidine

Prepared analogously to Example 2 from 2-chloro-4-diethylamino-8-methylthio-pyrimido[5,4-d]pyrimidine and piperazine in dimethylsulphoxide.
Yield: 69% of theory,
M.p.: 136° C. (methanol; sinters from 110° C.).

EXAMPLE 8

4-Di-n-propylamino-8-methylthio-2-piperazino-pyrimido-[5,4d]pyrimidine

Prepared analogously to Example 2 from 2-chloro-4-di-n-propylamino-8-methylthio-pyrimido[5,4-d]pyrimidine and piperazine in dimethylsulphoxide.
Yield: 95% of theory,
M.p.: 78°–80° C.

EXAMPLE 9

4-Di-n-butylamino-8-methylthio-2-piperazino-pyrimido[5,4-d]pyrimidine

Prepared analogously to Example 2 from 2-chloro-4-di-n-butylamino-8-methylthio-pyrimido[5,4-d]pyrimidine and piperazine in dimethylsulphoxide.
Yield: 42% of theory,
M.p.: 64°–70° C.

EXAMPLE 10

4-(N-Cyclohexyl-methylamino)-8-methylthio-2-piperazinopyrimido[5,4-d]pyrimidine

Prepared analogously to Example 2 from 2-chloro-4-(N-cyclohexyl-methylamino)-8-methylthiopyrimido[5,4-d]pyrimidine and piperazine in dimethylsulphoxide.
Yield: 64% of theory,
M.p.: 153°–154° C. (ethyl acetate).

EXAMPLE 11

4-(N-Benzyl-methylamino)-8-methylthio-2-piperazinopyrimido[5,4-d]pyrimidine

Prepared analogously to Example 2 from 2-chloro-4-(N-benzyl-methylamino)-8-methylthio-pyrimido[5,4-d]pyrimidine and piperazine in dimethylsulphoxide.
Yield: 45% of theory,
M.p.: 129°–131° C.

EXAMPLE 12

4-(N-Methyl-phenylamino)-8-methylthio-2-piperazinopyrimido[5,4-d]pyrimidine

Prepared analogously to Example 2 from 2-chloro-4-(N-methyl-phenylamino)-8-methylthio-pyrimido[5,4-d]pyrimidine and piperazine in dimethylsulphoxide.
Yield: 68% of theory,
M.p.: 126°–128° C.

EXAMPLE 13

4-(N-Ethyl-3'-hydroxy-n-propylamino)-8-methylthio-2-piperazino-pyrimido[5,4-d]pyrimidine Prepared analogously to Example 2 from 2-chloro-4-(N-ethyl-3'-hydroxypropylamino)-8-methylthiopyrimido[5,4-d]pyrimidine and piperazine in dimethylsulphoxide.
Yield: 55% of theory,
M.p.: 123°–125° C.

EXAMPLE 14

4-Methylamino-8-methylthio-2-piperazinopyrimido[5,4-d]pyrimidine

Prepared analogously to Example 2 from 2-chloro-4-methylamino-8-methylthio-pyrimido[5,4d]pyrimidine and piperazine in dimethylsulphoxide.
Yield: 70% of theory,
M.p.: 193°–194° C. (water).

EXAMPLE 15

4-n-Hexylamino-8-methylthio-2-piperazinopyrimido[5,4-d]pyrimidine

Prepared analogously to Example 2 from 2-chloro-4-n-hexylamino-8-methylthio-pyrimido[5,4-d]pyrimidine and piperazine in dimethylsulphoxide.
Yield: 95% of theory,
M.p.: 142°–144° C.

EXAMPLE 16

4-Heptamethyleneimino-8-methylthio-2-piperazinopyrimidino[5,4-d]pyrimidine

Prepared analogously to Example 2 from 2-chloro-4-heptamethyleneimino-8-methylthio-pyrimido[5,4-d]pyrimidine and piperazine in dimethylsulphoxide.
Yield: 82% of theory,
M.p.: 146°–148° C.

EXAMPLE 17

4-(N-Methyl-ethylamino)-8-methylthio-2-piperazinopyrimido[5,4-d]pyrimidine

Prepared analogously to Example 2 from 2-chloro-4-(N-methyl-ethylamino)-8-methylthio-pyrimido[5,4-d]pyrimidine and piperazine in dimethylsulphoxide.
Yield: 60% of theory,
M.p.: 207°–209° C.

EXAMPLE 18

4-Diallylamino-8-methylthio-2-piperazino-pyrimido[5,4-d]pyrimidine

Prepared analogously to Example 2 from 2-chloro-4-diallylamino-8-methylthio-pyrimido[5,4-d]pyrimidine and piperazine in dimethylsulphoxide.
Yield: 66% of theory,
Melting point of the hydrochloride: 178°–180° C.

The following compounds are obtained analogously to the preceding Examples:
4-Dimethyleneimino-8-methylthio-2-piperazino-pyrimido[5,4-d]pyrimidine
8-Methylthio-2-piperazino-4-trimethyleneimino-pyrimido[5,4-d]pyrimidine
8-Methylthio-4-octamethyleneimino-2-piperazino pyrimido[5,4-d]pyrimidine

EXAMPLE I

Coated tablets containing 4 mg of 8-methylthio-2-piperazino-4-pyrrolidino-pyrimido[5,4-d]pyrimidine Composition:
1 tablet core contains:

| | | |
|---|---|---|
| Active substance | (1) | 4.0 mg |
| Lactose | (2) | 27.0 mg |
| Corn starch | (3) | 14.5 mg |
| Polyvinylpyrrolidone | (4) | 4.0 mg |
| Magnesium stearate | (5) | 0.5 mg |
| | | 50.0 mg |

Preparation:
Substances 1–3 are uniformly moistened with an aqueous solution of 4, then passed through a 1 mm mesh screen, dried and again passed through a 1 mm mesh screen. After 5 has been mixed in, the mixture is compressed to form tablet cores.
Tablet cores: 5 mm O, biconvex, round
Coating:
Conventional sugar coating to give a finished weight of 70 mg.

EXAMPLE II

Tablets containing 8 mg of 8-methylthio-2-piperazino-4-pyrrolidino-pyrimido[5,4-d]pyrimidine 1 tablet contains:

| | |
|---|---|
| Active substance | 8.0 mg |
| Lactose | 23.0 mg |
| Corn starch | 14.5 mg |
| Polyvinylpyrrolidone | 4.0 mg |
| Magnesium stearate | 0.5 mg |
| | 50.0 mg |

Preparation:
Analogously to the cores for the coated tablets.
Description of tablet:
Weight: 50 mg
Diameter: 5 mm, biplanar, faceted on both sides

EXAMPLE III

Suppositories containing 25 mg of 8-methylthio-2-piperazino-4-pyrrolidino-pyrimido[5,4-d[pyrimidine 1 suppository contains:

| | |
|---|---|
| Active substance | 0.025 g |
| Hard fat (e.g. Witepsol H 19 and Witepsol H 45) | 1.675 g |
| | 1.700 g |

Preparation:

The hard fat is melted. At 38° C. the ground active substance is homogeneously dispersed in the melt. It is cooled to 35° C. and poured into slightly chilled suppository moulds. Weight of suppository: 1.7 g

EXAMPLE IV

Suspension containing 8 mg of 8-methylthio-2-piperazino-4-pyrrolidino-pyrimido[5,4-d[pyrimidine 100 ml of suspension contains:

| | |
|---|---|
| Active substance | 0.16 g |
| Carboxymethyl cellulose | 0.1 g |
| Methyl p-hydroxybenzoate | 0.05 g |
| Propyl p-hydroxybenzoate | 0.01 g |
| Glucose | 10.0 g |
| Glycerol | 5.0 g |
| 70% sorbitol solution | 20.0 g |
| Flavouring | 0.3 g |
| Distilled water | ad 100.0 ml |

Method of preparation:

The distilled water is heated to 70° C. The methyl and propyl p-hydroxybenzoates and the glycerol and carboxymethyl cellulose are dissolved therein with stirring. It is cooled to ambient temperature and the active substance is added and homogeneously dispersed therein with stirring. After the sugar, sorbitol solution and flavouring have been added and dissolved, the suspension is evacuated with stirring to eliminate air.

EXAMPLE V

Tablets containing 100 mg of 8-methylthio-2-piperazino-4-pyrrolidino-pyrimido[5,4-d]pyrimidine Composition:

1 tablet contains:

| | |
|---|---|
| Active substance | 100.0 mg |
| Lactose | 80.0 mg |
| Corn starch | 34.0 mg |
| Polyvinylpyrrolidone | 4.0 mg |
| Magnesium stearate | 2.0 mg |
| | 220.0 mg |

Method of preparation:

The active substance, lactose and starch are mixed together and uniformly moistened with an aqueous solution of the polyvinylpyrrolidone. After the moist mass has been screened (2.0 mm mesh) and dried in a rack-type drying cupboard at 50° C., it is screened again (1.5 mm mesh) and the lubricant is added. The mixture ready for compression is processed to form tablets.

Weight of tablet: 220 mg

Diameter: 10 mm, biplanar, faceted on both sides with a notch on one side.

EXAMPLE VI

Hard gelatine capsules containing b 150 mg of 8-methylthio-2-piperazino-4-pyrrolidino-pyrimido[5,4-d]pyrimidine 1 Capsule contains:

| | |
|---|---|
| Active substance | 150.0 mg |
| Dried corn starch | approx 180.0 mg |
| Powdered lactose | approx 87.0 mg |
| Magnesium stearate | 3.0 mg |
| | approx 420.0 mg |

Preparation:

The active substance is mixed with the adjuvants, passed through a 0.75 mm mesh screen and homogeneously mixed in a suitable apparatus. The final mixture is packed into size 1 hard gelatine capsules.

Capsule filling: about 320 mg

Capsule casing: hard gelatine capsule, size 1.

EXAMPLE VII

Suppositories containing 150 mg of 8-methylthio-2-piperazino-4-pyrrolidino-pyrimido[5,4-d]pyrimidine 1 suppository contains:

| | |
|---|---|
| Active substance | 150.0 mg |
| Polyethylene glycol 1500 | 550.0 mg |
| Polyethylene glycol 6000 | 460.0 mg |
| Polyoxyethylene sorbitan monostearate | 840.0 mg |
| | 2000.0 mg |

Preparation:

After the suppository mass has been melted, the active substance is homogeneously distributed therein and the melt is poured into chilled moulds.

EXAMPLE VIII

Suspension containing 50 mg of 8-methylthio-2-piperazino-4-pyrrolidino-pyrimido[5,4-d]pyrimidine 100 ml of suspension contains:

| | |
|---|---|
| Active substance | 1.0 g |
| Na salt of carboxymethyl cellulose | 0.1 g |
| Methyl p-hydroxybenzoate | 0.05 g |
| Propyl p-hydroxybenzoate | 0.01 g |
| Glucose | 10.0 g |
| Glycerol | 5.0 g |
| 70% sorbitol solution | 20.0 g |
| Flavouring | 0.3 g |
| Distilled water | ad 100 ml |

Preparation:

The distilled water is heated to 70° C. The methyl and propyl p-hydroxybenzoates and the glycerol and sodium salt of carboxymethyl cellulose are dissolved therein with stirring. It is cooled to ambient temperature and the active substance is added and homogeneously dispersed therein with stirring. After the sugar, sorbitol solution and flavouring have been added and dissolved, the suspension is evacuated with stirring to eliminate air.

5 ml of suspension contain 50 mg of active substance.

EXAMPLE IX

Tablets containing 150 mg of 8-methylthio-2-piperazino-4-pyrrolidino-pyrimido[5,4-d]pyrimidine Composition:
1 tablet contains:

| | |
|---|---|
| Active substance | 150.0 mg |
| Powdered lactose | 89.0 mg |
| Corn starch | 40.0 mg |
| Colloidal silicic acid | 10.0 mg |
| Polyvinylpyrrolidone | 10.0 mg |
| Magnesium stearate | 1.0 mg |
| | 300.0 mg |

Preparation:

The active substance mixed with the lactose, corn starch and silicic acid is moistened with a 20% aqueous polyvinylpyrrolidone solution and passed through a screen with a mesh size of 1.5 mm. The granulate dried at 45° C. is passed through the same screen again and mixed with the specified quantity of magnesium stearate. Tablets are compressed from the mixture.

Weight of tablet: 300 mg
Punch: 10 mm, flat

EXAMPLE X

Coated tablets containing 75 mg of 8-methylthio-2-piperazino-4-pyrrolidino-pyrimido[5,4-d]pyrimidine 1 tablet core contains:

| | |
|---|---|
| Active substance | 75.0 mg |
| Calcium phosphate | 93.0 mg |
| Corn starch | 35.5 mg |
| Polyvinylpyrrolidone | 10.0 mg |
| Hydroxypropyl methylcellulose | 15.0 mg |
| Magnesium stearate | 1.5 mg |
| | 230.0 mg |

Preparation:

The active substance is mixed with calcium phosphate, corn starch, polyvinylpyrrolidone, hydroxypropyl methylcellulose and half the specified quantity of magnesium stearate. Compressed tablets with a diameter of about 13 mm are produced in a tablet-making machine and these are then rubbed through a 1.5 mm mesh screen in a suitable apparatus and mixed with the remaining magnesium stearate. This granulate is compressed in a tablet-making machine to form tablets of the desired shape.

Weight of core: 230 mg
Punch: 9 mm, convex

The tablet cores thus produced are coated with a film consisting essentially of hydroxypropyl methylcellulose. The finished film-coated tablets are polished with beeswax.

Weight of coated tablet: 245 mg.

Obviously, all the other compounds of general formula I may be used as active substances in the galenic preparations described hereinbefore.

What is claimed is:

1. An 8-alkylthio-2-piperazino-pyrimido[5,4-d]pyrimidine of the formula:

(I)

wherein
$R_1$ is alkyl group having 1 to 3 carbon atoms;
$R_2$ is a hydrogen atom, an allyl group or an alkyl group having 1 to 4 carbon atoms;
$R_3$ is an alkyl group having 1 to 6 carbon atoms or an allyl, cyclohexyl, phenyl, benzyl, 2-hydroxyethyl, 2-hydroxy-n-propyl or 3-hydroxy-n-propyl group; or
$R_2$ and $R_3$ together with the nitrogen atom between them form a pyrrolidino, piperidino, hexamethyleneimino or heptamethyleneimino group;
or a physiologically acceptable acid addition salt thereof.

2. An 8-alkylthio-2-piperazino-pyrimido[5,4-d]pyrimidine of formula I as claimed in claim 1, wherein
$R_1$ is a methyl group,
$R_2$ is a hydrogen atom or a methyl or ethyl group,
$R_3$ is an alkyl group having 1 to 6 carbon atoms or
$R_2$ and $R_3$ together with the nitrogen atom between them form a pyrrolidino, piperidino, hexamethyleneimino or heptamethyleneimino group or a physiologically acceptable acid addition salt thereof.

3. An 8-alkylthio-2-piperazino-pyrimido[5,4-d]pyrimidine of formula I as claimed in claim 1, wherein
$R_1$ is a methyl group and
$R_2$ and $R_3$ together with the nitrogen atom between them form a dimethylamino, diethylamino, pyrrolidino, piperidino or hexamethyleneimino group,
or a physiologically acceptable acid addition salt thereof.

4. In accordance with claim 1, 8-methylthio-2-piperazino-4-pyrrolidino-pyrimido[5,4-d]pyrimidine or a physiologically acceptable acid addition salt thereof.

5. A pharmaceutical composition for the prophylaxis of thromboembolic diseases, arteriosclerosis, metastasis, and for inhibiting tumor growth, comprising a pharmaceutically acceptable carrier and a therapeutically effective amount of a compound in accordance with claim 1, 2, 3 or 4.

* * * * *